United States Patent [19]

Imamura et al.

[11] Patent Number: 4,845,028
[45] Date of Patent: Jul. 4, 1989

[54] COMPOSITION FOR LIPASE ASSAY

[75] Inventors: Shigeyuki Imamura; Hideo Misaki, both of Shizuoka, Japan

[73] Assignee: Toyo Jozo Kabushiki Kaisha, Shizuoka, Japan

[21] Appl. No.: 244,513

[22] Filed: Sep. 9, 1988

Related U.S. Application Data

[63] Continuation of Ser. No. 906,689, Sep. 11, 1986, abandoned, which is a continuation-in-part of Ser. No. 554,028, Nov. 21, 1983, abandoned.

[30] Foreign Application Priority Data

Nov. 19, 1982 [JP] Japan ................. 57-203873

[51] Int. Cl.$^4$ .................... C12Q 1/48; C12Q 1/00; C12Q 1/34; C12Q 1/44
[52] U.S. Cl. ........................... 435/15; 435/4; 435/18; 435/19; 435/25; 435/26; 435/21
[58] Field of Search ................... 435/4, 15, 18, 19, 21, 435/25, 26, 28

[56] References Cited

U.S. PATENT DOCUMENTS

| | | | |
|---|---|---|---|
| 4,241,178 | 12/1980 | Esders et al. | 435/15 |
| 4,491,631 | 1/1985 | Imamura et al. | 435/15 X |
| 4,555,483 | 11/1985 | LiMuti et al. | 435/19 |

FOREIGN PATENT DOCUMENTS 57-91197 6/1982 Japan ................. 435/4

OTHER PUBLICATIONS

Chem. Abs., 93:233,542p, (1980).
Garland et al., Nature, 196:987–988, Oct. 6, 1982.
Hagen et al., Can. J. Biochem. Phys., 40:1129–1139, (1962).

*Primary Examiner*—Esther M. Kepplinger
*Attorney, Agent, or Firm*—Young & Thompson

[57] ABSTRACT

A composition and method for lipase assay, comprising the use of an aqueous solution of a 1,2-diglyceride of a higher fatty acid, and a nonionic surface active agent. The higher fatty acid is a higher fatty acid of 8 or more and preferably 12 or more carbons, most preferably a higher unsaturated fatty acid of more than 16 carbons. The concentration of 1,2-diglyceride is more than 0.5 g per liter of solution. The nonionic surface active agent is a polyoxyethylene-type nonionic surface active agent, a polyhydric-alcohol-type nonionic surface active agent or a block-polymer-type nonionic surface active agent, whose concentration is more than 0.1% by weight in the composition and which has an HLB more than 10. The composition preferably contains 0.5–10 g of 1,2-diglyceride and 10–50 g of nonionic surface active agent per liter of solution.

11 Claims, No Drawings

COMPOSITION FOR LIPASE ASSAY

This application is a continuation of application Ser. No. 906,689, filed September 11, 1986, now abandoned. Which is a continuation-in-part application of our copending application Ser. No. 554,028 filed Nov. 21, 1983, now abandoned.

This invention relates to an assay method for lipase activity. More particularly the invention pertains to an assay method for lipase activity which comprises contacting a specimen with homogeneous solution containing a 1,2-diglyceride of a higher fatty acid, and a nonionic surface active agent, and measuring the thus liberated substance.

Heretofore, in the assay of lipase activity from the pancreas, triglyceride has been used as a substrate. Lipase has also been known to decompose monoglycerides and diglycerides.

Lipase activity has been measured by emulsifying an olive oil, mainly containing triglycerides, by adding gum arabic or polyvinyl alcohol in water to prepare an emulsion, and titrating the acidity of liberated free fatty acid derived by lipase action. Such an emulsion, however, could not be used for the spectrometric measurement of lipase activity due to the turbidity of the emulsion. Also, such a composition has the disadvantage of phase separation upon long term storage, and therefore lipase assays could not be performed with good reproducibility.

Assay methods of free fatty acid, for example, a titration method of the acidity of fatty acid, and a method comprising treating copper salt extractions of fatty acid with a copper reagent [Clinical Assay: 15 (2): 191, 1971], and a spectrometric measurement method using acyl-CoA oxidase [In summary, Congress of Japan. Agr. Chēm. Soc., page 38, 1980] are also known.

Furthermore, a spectrometric assay method using acyl-CoA synthetase, acyl-CoA oxidase, enoyl-CoA hydratase, 3-hydroxyacyl-CoA dehydrogenase and 3-ketoacyl-CoA thiolase is known as an assay method of fatty acid for lipase assay. [Jap. Pat. Appln. No. 56-148313]. A method measuring the glycerol liberated from substrate triglyceride is also known. [Nature, 196: 987–988, 1962, Biochem. Z., 329: 313, 1957, Can. J. Biochem. Biophys., 40: 1129, 1962, U.S. Pat. No. 4,241,178].

These assay methods for free fatty acid can be used for lipase assay; however, as explained hereinbefore, since the substrate composition for lipase assay is an emulsion, there are a number of disadvantages.

We have found that an assay method for lipase activity can be made by using a composition comprising a 1,2-diglyceride of a higher fatty acid of 8 or more and preferably 12 or more carbons, solubilized in water using a nonionic surface active agent, and the said composition can be stored for long periods with good stability, can be used for spectrometric measurements due to its water soluble form, and is useful for lipase assay with good reproducibility.

An object of the present invention is to provide an assay method for lipase activity comprising contacting a specimen with homogeneous solution containing a 1,2-diglyceride of a higher fatty acid, and a nonionic surface active agent.

Suitable 1,2-diglycerides of higher fatty acids are compounds of the formula [I]

wherein $R_1$ is a higher fatty acid residue and $R_2$ is a higher fatty acid residue.

Suitable higher fatty acid residues $R_1$ or $R_2$ are fatty acids of 8 or more and preferably 12 or more carbons. Examples of saturated higher fatty acids are lauric acid ($C_{12:0}$), tridecylenic acid ($C_{13:0}$), myristic acid ($C_{14:0}$), pentadecylenic acid ($C_{15:0}$), palmitic acid ($C_{16:0}$), margaric acid ($C_{17:0}$), stearic acid ($C_{18:0}$), nonadecylenic acid ($C_{19:0}$) arachidic acid ($C_{20:0}$), behenic acid ($C_{21:0}$) and lignoceric acid ($C_{22:0}$). Examples of unsaturated higher fatty acids are palmitoleic acid ($C_{16:1}$), 9-octadecenic acid ($C_{18:1}$; oleic acid), 11-octadecenic acid ($C_{18:1}$; bacucenic acid), 12-octadecenoic acid ($C_{18:1}$), 9-eicosanoic acid ($C_{20:1}$), 11-eicosanoic acid ($C_{20:1}$), 11-decosanoic acid ($C_{22:1}$), 13-docosanoic acid ($C_{22:1}$; erucic acid), linolic acid ($C_{18:2}$), linolenic acid ($C_{18:3}$), 11,14-eicosadienoic acid ($C_{20:2}$), 8,11,14-eicosatrienoic acid ($C_{20:3}$) or 5,8,11, 14-eicosatetraenoic acid ($C_{20:4}$; arachiodic acid). Glycerides wherein $R_1$ and $R_2$ are unsaturated fatty acids are preferred because of the resulting clear solution. Preferred 1,2-diglycerides are glycerides having at least one unsaturated fatty acid residue of 8 or more carbons. 1,2-diglycerides wherein one of $R_1$ and $R_2$ is an unsaturated higher fatty acid residue and the other is a saturated higher fatty acid residue, are preferred.

The most preferred examples are 1,2-diglycerides wherein $R_1$ is an unsaturated higher fatty acid ($C_{16:1}$, $C_{18:1}$, $C_{20:1}$, $C_{22:1}$, $C_{18:2}$, $C_{18:3}$, $C_{20:2}$, $C_{20:3}$ or $C_{20:4}$) residue and $R_2$ is a saturated higher fatty acid ($C_{8:0}$, $C_{10:0}$, $C_{12:0}$, $C_{14:0}$, $C_{16:0}$, $C_{18:0}$ or $C_{20:0}$) residue or an unsaturated higher fatty acid ($C_{16:1}$, $C_{18:1}$, $C_{22:1}$, $C_{22:1}$, $C_{18:2}$, $C_{18:3}$, $C_{20:2}$, $C_{20:3}$ or $C_{20:4}$) residue. Examples of these 1,2-diglycerides are 1-caprylyl-2-decenoylglycerol, 1-decenoyl-2-caprylylglycerol, 1-caprylyl-2-dodecenoylglycerol, 1-docenoyl-2-caprylylglycerol, 1-caprylyl-2-palmitolelglycerol, 1-palmitoleyl-2-caprylylglycerol, 1-caprylyl-2-oleoylglycerol, 1-oleoyl-2-caprylylglycerol, 1-caprylyl-2-linoleoylglycerol, 1-linoleoyl-2-caprylyl-glycerol, 1-caprylyl-2-linolenoylglycerol, 1-linolenoyl-2-caprylylglycerol, 1-capryl-2-decenoylglycerol, 1-decenoyl-2-caprylglycerol, 1-capryl-2-dodecenoylglycerol, 1-dodece-noyl-2-caprylglycerol, 1-capryl-2-palmitoleylglycerol, 1-palmitoleyl-2-capryl-glycerol, 1-capryl-2-oleyglycerol, 1-oleyl-2-capryl-glycerol, 1-capryl-2-linoleoylglycerol, 1-linoleoyl-2-caprylglycerol, 1-capryl-2-linoleoylglycerol, 1-linolen-oyl-2-caprylglycerol, 1-palmitoleoyl-2-lauroyl-glycerol, 1-palmitoleoyl-2-palmitoyl-glycerol, 1-oleoyl-2-palmitoyl-glycerol, 1-linoleoyl-2-lauroyl-glycerol, 1-lino-leoyl-2-myristoyl-glycerol, 1-linoleoyl-2-palmitoyl-glycerol, 1-linoleoyl-2-stearoyl-glycerol, 1-linolen-oyl-2-lauroyl-glycerol, 1-linolenoyl-2-myristoyl-glycerol, 1-lino-lenoyl-2-palmitoyl-glycerol, 1-linolen-oyl-2-stearoyl-glycerol, 1-(11,14-eicosenoyl)-2-myristoyl-glycerol, 1-(11,14-eicosenoyl)-2-plamitoyl-glycerol, 1-(8,11,14,17-eicosatetraenoyl)-2-lauroyl-glycerol, 1-(8,11,14,17-eicosatetraenoyl)-2-palmitoyl-glycerol, 1,2-dilinoleoyl-glycerol, 1,2-dilinoleoyl-glycerol and 1,2-dilinolenoyl-glycerol.

The 1,2-diglycerides can also be obtained as follows:

For example, 1,2-diglycerides can be prepared by reacting lecithin with phospholipase C, phosphatidic acid with phosphatidate phosphatase, or lecithin with phospholipase D and phosphatidate phosphatase. The 1,2-diglycerides can be used directly without isolation and purification, for example, a reaction mixture of phospholipase C and lecithin, or other reaction mixture producing a 1,2-diglyceride, can also be used.

Examples of nonionic surface active agents are as follows:

Polyoxyethylene (POE) aliphatic alcohols:
EMULGEN 106 (Kao Atlas Co., POE lauryl alcohol ether: HLB 10.5)
EMULGEN 108 (POE lauryl alcohol ether: HLB 12.1)
EMULGEN 220 (POE cetyl alcohol ether: HLB 14.2)
EMULGEN 408 (POE oleyl alcohol ether: HLB 10.0)
Brij 35 (POE (23) lauryl alcohol ether: HLB 16.9)
Brij 78 (POE (20) stearyl alcohol ether: HLB 15.3)
Brij 98 (POE (120) oleyl alcohol ether: HLB 15.3)
EMULGEN 340 (POE stearyl ether: HLB 17.3)
NONIOLITE AL-11 (Kyoeisha Yushi Co., POE lauryl ether: HLB 14.0)
NONIOLITE AO-20 (POE oleyl ether: HLB 15.4)
NIKKOL BB-20 (Nikko Chem. Co., POE behenyl ether: HLB 17),
NIKKOL BL-9EX, BO-10TX, BC-15TX, BH-5
EMULEX BA 10 (Nippon Emulsion Co., POE butyl alcohol ether: HLB 16.9)
EMULEX BA 15 (POE butyl alcohol ether: HLB 18.7)
EMULEX 130 (POE cetyl alcohol ether: HLB 16.0)
EMULEX 100 (POE cetyl alcohol ether: HLB 14.5)
EMULEX 550 (POE oleyl alcohol ether: HLB 18.2)
EMULEX 700 (POE lauryl alcohol ether: HLB 16.7)
NONION E-213 (Nippon Yushi Co., POE oleyl alcohol ether: HLB 13.6)
NONION E-220 (POE oleyl alcohol ether: HLB 15.3)
NONION P-225 (POE cetyl alcohol ether: HLB 16.4)
NONION S-215 (POE stearyl alcohol ether: HLB 14.2)
NONION T-208.5 (POE tridecyl alcohol ether: HLB 13.0)
LIPONOX OCS (Lion Yushi Co., POE alkyl ether: HLB 15.0)
LIPONOX LCR (POE alkyl ether: HLB 16.2)
LIPONOX O (POE alkyl ether: HLB 14.3)
Adekatol SO-120 (Asahi Denka Co., POE sec-straight chain alcohol ethoxylate),
Adekatol SO-145 (POE sec-straight chain alcohol ethoxylate)
Adekatol LO-9 (POE primary straight chain alcohol ethoxylate)
Adekatol LO-15 (POE primary straight chain alcohol ethoxylate)

POE alkylaryl ethers:
EMULGEN 810 (Kao Atlas Co., POE octyl phenyl ether: HLB 13.1)
EMULGEN 911 (POE nonyl phenyl ether: HLB 13.7)
EMULGEN 930 (POE nonyl phenyl ether: HLB 15.1)
EMULGEN 950 (POE nonyl phenyl ether: HLB 18.2)
NONIOLITE PO-9 (Kyoeisha Yushi Co., POE octyl phenyl ether: HLB 13.2)
NONIOLITE PA-15 (POE alkyl phenyl ether: HLB 14.3)
EMULEX NP-15 (Nippon Emulsion Co., POE alkyl phenol ether: HLB 13.2)
EMULEX OP-25 (POE alkyl phenol ether: HLB 15.8)
NONION NS-215 (Nippon Yushi Co., POE nonyl phenol ether: HLB 15.0)
NONION NS-220 (POE nonyl phenol ether: HLB 16.0)
NONION HS-212 (POE octyl phenol ether: HLB 14.4)
NONION HS-220 (POE octyl phenol ether: HLB 16.2)
LIPONOX NCM (Lion Yushi Co., POE alkyl phenol ether: HLB 14.5)
LIPONOX NCN (POE alkyl phenol ether: HLB 14.8)
LIPONOX NCO (POE alkyl phenol ether: HLB 15.0)
Nonidet P-40 (Shell Oil Co., POE alkyl aryl ether)
Triton X-100 (Rhom & Haas Co., POE alkyl aryl ether)
NIKKOL NP-10 (Nikko Chem. Co.), NP-18 TX, NP-20, OP-40

POE fatty acid esters:
EMANON 1112 (Kao Atlas Co., POE monolaurate: HLB 13.7)
EMANON 4115 (POE monooleate: HLB 13.4)
Myrj 45 (POE(8) stearate: HLB 11.1)
Myrj 52 (POE(40) stearate: HLB 16.9)
Myrj 53 (POE(50)stearate: HLB 17.9)
NONIOLITE S-100 (Kyoeisha Yushi Co., POE stearate: HLB 15.6)
NONIOLITE T-40 (POE tall oil fatty acid ester: HLB 11.5)
EMULEX 202 (Nippon Emulsion Co., POE oleate: HLB 15.1)
EMULEX 203 (POE oleate: HLB 10.6)
EMULEX 800 (POE monolaurate: HLB 15.8)
NONION P-10 (POE monopalmitate: HLB 15.7)
NONION S-10 (POE monostearate: HLB 15.2)
NONION S-40 (POE monostearate: HLB 18.2)
MYL-10, MYO-10 (Nikko Chem. Co.)

POE sorbitan fatty acid esters:
EMASOL 1130 (Kao Atlas Co., POE sorbitan monolaurate: HLB 16.3)
EMASOL 3130 (POE sorbitan monostearate: HLB 14.9)
Tween 20 (POE(20)sorbitan monolaurate: HLB 16.7)
Tween 40 (POE(20) sorbitan monopalmitate: HLB 15.6)
Tween 80 (POE(20) sorbitan monooleate: HLB 15.0)
NONIOLITE TWL-20 (Kyoeisha Yushi Co., POE(20-)sorbitan monolaurate: HLB 16.2)
NONIOLITE TWS-13 (POE(13) sorbitan monostearate: HLB 12.5)
SOLGEN TW-20 (Daiichi Kogyo Seiyaku Co., POE sorbitan monolaurate: HLB 16.7)
SOLGEN TW-80 (POE sorbitan monooleate: HLB 15.0)
NIKKOL TSDL-2020L (Nikko Chem. Co., POE sorbitan olive oil fatty acid: HLB 16.5)
TL-10, TO-106
EMULEX ET-2000 (Nippon Emulsion Co., POE sorbitan laurylate: HLB 16.6)
NONION LT-221 (Nippon Yushi Co., POE sorbitan laurylate: HLB 16.7)
NONION ST-221 (POE sorbitan stearate: HLB 14.9)
NONION OT-221 (POE sorbitan oleate: HLB 15.0)
Sorbon T-20 (Toho Chem. Co., POE sorbitan monolaurate: HLB 16.7)
Sorbon T-40 (POE sorbitan monopalmitate: HLB 15.7)
Sorbon T-80 (POE sorbitan monooleate: HLB 15.0)

POE sorbitol fatty acid esters:
Atlox 1045 A (Kao Atlas Co., POE sorbitol oleate laurate: HLB 13.2)
Atlox 1196 (POE sorbitol oleate: HLB 11.4)
G-1045 (POE sorbitol laurate: HLB 11.5)
G-1045 (POE sorbitol lanolin derivative: HLB 14)
NIKKOL TSOL-1020L (Nikko Chem. Co., POE sorbitol olive oil fatty acid ester: HLB 16.0)
GL-1

POE castor oil derivative and POE-hardened castor oil derivatives:

G-1288 (Kao Atlas Co., castor oil ethyleneoxide additive: HLB 16.0)
G-1295 (hardened castor oil ethyleneoxide additive: HLB 17.5)
G-1292 (hardened castor oil ethyleneoxide additive: HLB 10.8)
NIKKOL CO-60TX (Nikko Chem. Co., POE(60) castor oil: HLB 14).

POE glycerol fatty acid esters:

NIKKOL TGSO 215 (Nikko Chem. Co., POE glycerol vegetable oil fatty acid ester: HLB 14).
TGSO 220 (POE glycerol vegetable oil fatty acid ester: HLB 15.5)
TDGOL-2010 (POE diglycerol olive oil fatty acid ester: HLB 12.5)

POE lanolin derivatives:

G-1790 (Kao Atlas Co.)
G-1795 (Kao Atlas Co.)
BWA-5 (Nikko Chem. Co.)

POE-type nonionic surface active agents such as POE alkylthio ethers and POE prolyleneglycol mono fatty acid esters; Block-type nonionic surface active agents consisting of polyoxypropylene blocks and POE blocks;

Pluronic L 121, L 122 (Asahi Denka Kogyo Co.) Polyhydric-alcohol-type nonionic surface active agents comprising esters of polyhydric alcohols of more than 6 carbons such as sorbitan, mannitol, sorbitol and sucrose, and higher fatty acids of more than 12 carbons such as lauric acid, palmitic acid, stearic acid, isostearic acid and other natural fatty acids.

Among these nonionic surface active agents, the preferred combination is a 1,2-diglyceride and a POE alkylaryl ether series surface active agent or a block-type nonionic surface active agent.

Further preferred nonionic surface active agents are generally of HLB more than 10, preferably of HLB more than 11, and can be given an HLB higher than 10 by using jointly two or more nonionic surface active agents.

A composition can be prepared by adding an aliquot amount of a 1,2-diglyceride to a 1–5 w/w % aqueous solution of nonionic surface active agent with heating. 5–100 parts by weight of the 1,2-diglyceride is mixed with 100–500 parts by weight of the nonionic surface active agent. The aqueous composition may preferably contain 0.5–10 g of 1,2-diglyceride and 10–50 g of nonionic surface active agent per 1 lit. of solution.

The said composition can be used directly as a substrate of lipase assay, and a suitable reagent for the fatty acid or glycerol which is liberated by lipase action can also be added to the composition.

Reagents which can be added therein are known reagents for fatty acids or glycerol.

Thus, a compound of formula [I] which is contained in the composition is decomposed by lipase action to liberate a fatty acid and glycerol. (Reaction [II])

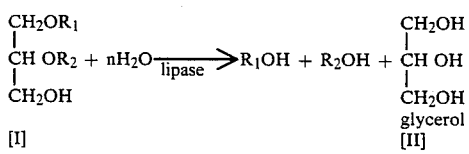

wherein R$_1$ and R$_2$ are higher fatty acid residues.

Examples of assay methods of liberated fatty acid R$_1$OH (specifically: R$_1$'COOH) and R$_2$OH (R$_2$: higher fatty acid residue, specifically, R$_2$'COOH) (hereinafter these are designated as RCH$_2$CH$_2$COOH) are illustrated as follows:

The following abbreviations are used:

AMP: adenosine monophosphate, RCH$_2$CH$_2$COSCoA: acyl coenzyme A, RCH=CHCOSCoA: 2,3-dehydroacyl coenzyme A,

hydroxyl acyl coenzyme A, RCOCH$_2$COSCoA: 3-ketoacyl coenzyme A, ADP: adenosine diphosphate, ITP: inosine triphosphate, CoASH: coenzyme A.

(1) A method using ATP, CoASH, acyl-CoA synthetase (EC:6.2.1.3) and acyl-CoA oxidase (U.S. Pat. No. 4,340,173):

Process a:

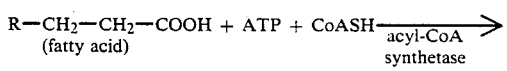

$$R-CH_2-CH_2-\overset{O}{\underset{\|}{C}}-SCoA + AMP + PPi$$
(acyl-CoA)

Process b:

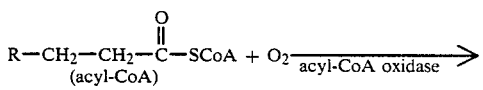

$$R-CH=CH-\overset{O}{\underset{\|}{C}}-SCoA + H_2O_2$$
(dehydroacyl-CoA)

Process c: measuring consumed O$_2$ or generated H$_2$O$_2$.

(2) A method using ATP, CoASH, acyl-CoA synthetase, acyl-CoA oxidase, enoyl-CoA hydratase (EC 4.2.1.17), 3-hydroxy-CoA dehydrogenase (EC 1.1.1.35), 3-ketoacyl-CoA thiolase (EC 2.3.1.16) NAD+ and optionally catalase; or using multi-active enzyme for enoyl-CoA hydratase, 3-hydroxy CoA dehydrogenase and 3-ketoacyl-CoA thiolase in place of the above three enzymes (for example, an enzyme obtained from *Pseudomonas fragi* B-0771 FERM-P No. 5701: U.K. Pat. Appln. 8218552):

Process a:

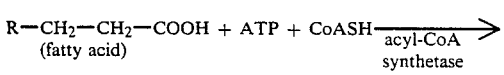

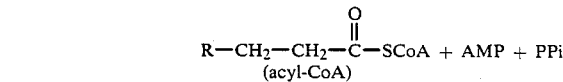

Process b:

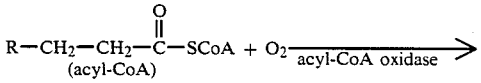

-continued $$R-CH=CH-\overset{O}{\underset{\|}{C}}-SCoA + H_2O_2$$
(dehydroacyl-CoA)

Process c:

$$R-CH=CH-\overset{O}{\underset{\|}{C}}-SCoA + H_2O \xrightarrow{\text{enoyl-CoA hydratase}}$$
(dehydroacyl-CoA)

$$R-\overset{OH}{\underset{|}{CH}}-CH_2-\overset{O}{\underset{\|}{C}}-SCoA$$
(hydroxyacyl-CoA)

Process d:

$$R-\overset{OH}{\underset{|}{CH}}-CH_2-\overset{O}{\underset{\|}{C}}-SCoA + NAD \xrightarrow[\text{dehydrogenase}]{\text{3-hydroxyacyl-CoA}}$$

$$R-\overset{O}{\underset{\|}{C}}-CH_2-\overset{O}{\underset{\|}{C}}-SCoA + \text{reduced NAD}$$

Process e:

$$R-\overset{O}{\underset{\|}{C}}-CH_2-\overset{O}{\underset{\|}{C}}-SCoA + CoASH \xrightarrow[\text{thiolase activity}]{\text{3-ketoacyl-CoA}}$$
(ketoacyl-CoA)

$$R-\overset{O}{\underset{\|}{C}}-SCoA + CH_3\overset{O}{\underset{\|}{C}}-SCoA$$
(acyl-CoA)

Process f: (RCOSCoA generated in process e is subjected to a cycling reaction in the process b reaction)

measuring consumed $O_2$, generated $H_2O_2$ or reduced NAD.

(3) A method using ATP, CoASH, acyl-CoA synthetase, myokinase (EC 2.7.4.3), MgCl$_2$, phosphoenolpyruvate (PEP), pyruvate kinase (Ec 2.7.1.40), reduced NAD and L-lactate dehydrogenase (EC 1.1.1.27):

Process a:

$$R-CH_2-CH_2-COOH + ATP + CoASH \xrightarrow[\text{synthetase}]{\text{acyl-CoA}}$$
(fatty acid)

$$R-CH_2-CH_2-\overset{O}{\underset{\|}{C}}-SCoA + AMP + PPi$$
(acyl-CoA)

Process b:

$$AMP + ATP \xrightarrow{\text{myokinase}} 2\ ADP$$

Process c:

$$2\ ADP + 2\ PEP \xrightarrow{\text{pyruvate kinase}} 2\ ATP + 2\ \text{pyruvate}$$

Process d:

$$2\ \text{pyruvate} + 2\ \text{reduced NAD} \xrightarrow{\text{L-lactate dehydrogenase}}$$

$$2\ \text{L-Lactate} + 2\ NAD^+$$

Process e: measuring consumed reduced NAD.

(4) A method using pyruvate oxidase (EC 1.2.3.3) in place of reduced NAD and lactate dehydrogenase in the above processes:

Process d:

$$2\ \text{pyruvate} + 2\ O_2 \xrightarrow{\text{pyruvate oxidase}}$$

$$2\ \text{acetylphosphate} + 2\ CO_2 + 2H_2O_2$$

(5) A method using ATP, CoASH, acyl-CoA synthetase and AMP deaminase (EC 3.5.4.6):

Process a:

$$R-CH_2-CH_2-COOH + ATP + CoASH \xrightarrow[\text{synthetase}]{\text{acyl-CoA}}$$
(fatty acid)

$$R-CH_2-CH_2-\overset{O}{\underset{\|}{C}}-SCoA + AMP + PPi$$

Process b:

$$AMP + H_2O \xrightarrow{\text{AMP deaminase}} 5'\text{-inocinate} + NH_3$$

Process c: measuring generated $NH_3$.

(6) A method using ATP, CoASH, acyl CoA synthetase, AMP nucleosidase (EC 3.2.2.4) and adenine deaminase (EC 3.5.4.2):

Process a:

$$R-CH_2-CH_2-COOH + ATP + CoASH \xrightarrow[\text{synthetase}]{\text{acyl-CoA}}$$
(fatty acid)

$$R-CH_2-CH_2-\overset{O}{\underset{\|}{C}}-SCoA + AMP + PPi$$

Process b:

$$AMP + H_2O \xrightarrow{\text{AMP nucleosidase}}$$

$$\text{adenine} + \text{D-ribose-5'-phosphate}$$

Process c:

$$\text{adeneine} + H_2O \xrightarrow{\text{adenine deaminase}} \text{hypoxanthine} + NH_3$$

Process d: measuring generated $NH_3$.

(7) A method using ATP, CoASH, acyl-CoA synthetase, myokinase, magnesium chloride, and ADP deaminase (EC 3.5.4.7):

Process a:

-continued $$R-CH_2-CH_2-COOH + ATP + CoASH \xrightarrow[\text{synthetase}]{\text{acyl-CoA}}$$
(fatty acid)

$$R-CH_2-CH_2-\overset{\overset{O}{\|}}{C}-SCoA + AMP + PPi$$
(acyl-CoA)

Process b:

$$AMP + ATP \xrightarrow{\text{myokinase}} 2\ ADP$$

Process c:

$$2\ ADP + 2\ H_2O \xrightarrow{\text{ADP deaminase}} 2\ IDP + 2\ NH_3$$

Process d: measuring generated $NH_3$.

(8) A method using ATP, CoASH, acyl-CoA synthetase, myokinase, magnesium chloride, GTP-adenylate kinase (EC 2.7.4.10), inosine diphosphate (IPP), hexokinase (EC 2.7.1.1), glucose-6-phosphate dehydrogenase (EC 1.1.1.45) and $NADP^+$:

Process a:

$$R-CH_2-CH_2-COOH + ATP + CoASH \xrightarrow[\text{synthetase}]{\text{acyl-CoA}}$$
(fatty acid)

$$R-CH_2-CH_2-\overset{\overset{O}{\|}}{C}-SCoA + AMP + PPi$$
(acyl-CoA)

Process b:

$$AMP + ATP \xrightarrow{\text{myokinase}} 2\ ADP$$

Process c:

$$2\ ADP + 2\ IDP \xrightarrow{\text{GTP-adenylate kinase}} 2\ AMP + 2\ ITP$$

Process d:

$$2\ ITP + 2\ \text{glucose} \xrightarrow{\text{hexokinase}} 2\ \text{glucose-6-phosphate} + 2\ IDP$$

Process e:

$$2\ \text{glucose-6-phosphate} + 2\ NADP^+ \xrightarrow{\text{glucose-6-phosphate dehydrogenase}}$$

$$2\text{-glucono-}\delta\text{-lactone-6-phosphate} + 2\ \text{reduced NADP}$$

Process f: measuring generated reduced NADP.

(9) A method using ATP, CoASH, acyl-CoA synthetase, AMP pyrophosphorilase (EC 2.4.2.7), AMP and adenine deaminase:

Process a:

$$R-CH_2-CH_2-COOH + ATP + CoASH \xrightarrow[\text{synthetase}]{\text{acyl-CoA}}$$
(fatty acid)

$$R-CH_2-CH_2-\overset{\overset{O}{\|}}{C}-SCoA + AMP + PPi$$
(acyl-CoA)

Process b:

$$\text{pyrophosphate} + AMP \xrightarrow{\text{AMP pyrophosphorilase}}$$

$$\text{adenine} + \text{5-phospho-D-ribosylpyrophosphate}$$

Process c:

$$\text{adenine} + H_2O \xrightarrow{\text{adenine deaminase}} \text{hypoxanthine} + NH_3$$

Process d: measuring generated $NH_3$.

Further assay methods for glycerol liberated from a compound [I] are illustrated as follows:

(10) A method using magnesium chloride, ATP, glycerol kinase (EC 2.7.1.30) and glycerophosphate oxidase (U.S. Pat. Nos. 4,166,005 and 4,275,161):

Process a:

$$\text{glycerol} + ATP \xrightarrow[\text{kinase}]{\text{glycerol}} \text{glycerol-3-phosphate} + ADP$$

Process b:

$$\text{glycero-3-phosphate} + O_2 \xrightarrow{\text{glycerophosphate oxidase}}$$

$$\text{dihydroxyacetone phosphate} + H_2O_2$$

Process c: measuring consumed $O_2$ or generated $H_2O_2$.

(11) A method using magnesium chloride, ATP, glycerol kinase, glycerophosphate dehydrogenase (EC 1.1.99.5) and hydrogen acceptor (phenazine methosulfate, etc.):

Process a:

$$\text{glycerol} + ATP \xrightarrow[\text{kinase}]{\text{glycerol}} \text{glycero-3-phosphate} + ADP$$

Process b:

glycero-2-phosphate +

$$\text{phenazine methosulfate (PMS)} \xrightarrow{\text{glycerophosphate dehydrogenase}}$$

$$\text{dihydroxyacetone phosphate} + \text{reduced PMS}$$

Process c:

$$\text{reduced PSM} + \tfrac{1}{2} O_2 \longrightarrow PMS + H_2O$$

Process d: measuring consumed $O_2$.

(12) A method using glycerol dehydrogenase (EC 1.1.1.6) and $NAD^+$:

Process a:

glycerol + NAD⁺ $\xrightarrow{\text{glycerol dehydrogenase}}$ dihydroxyacetone + reduced NAD Process b: measuring generated reduced NAD.

(13) A method using magnesium chloride, ATP, glycerol kinase, PEP, pyruvate kinase and pyruvate oxidase:

Process a:

glycerol + ATP $\xrightarrow{\text{glycerol kinase}}$ glycero-3-phosphate + ADP

Process b:

ADP + PEP $\xrightarrow{\text{pyruvate kinase}}$ pyruvate + ATP

Process c:

pyruvate + O₂ $\xrightarrow{\text{pyruvate oxidase}}$ acetyl phosphate + CO₂ + H₂O₂

Process d:

measuring consumption of O₂, or measuring generated CO₂ or H₂O₂.

(14) A method using magnesium chloride, ATP, glycerol kinase, PEP, pyruvate kinase, L-lactate dehydrogenase and reduced NAD:

Process a:

glycerol + ATP $\xrightarrow{\text{glycerol kinase}}$ glycero-3-phosphate + ADP

Process b:

ADP + PEP $\xrightarrow{\text{pyruvate kinase}}$ pyruvate + ATP

Process c:

pyruvate + reduced NAD $\xrightarrow{\text{lactate dehydrogenase}}$ L-lactate + NAD⁺

Process d: measuring consumed reduced NAD.

(15) A method using magnesium chloride, ATP, glycerol kinase and ADP deaminase:

Process a:

glycerol + ATP $\xrightarrow{\text{glycerol kinase}}$ glycero-3-phosphate + ADP

Process b:

ADP + H₂O $\xrightarrow{\text{ADP deaminase}}$ IDP + NH₃

Process c: measuring generated NH₃.

In the above methods, pyruvate generated in processes (3)c, (13)b and (14)b can be assayed by reacting with a hydrazine, such as 2,4-dinitrophenylhydrazine, to generate pigment having maximum absorption at 440 nm, and the hydrogen acceptor, phenazine methosulfate, can be replaced by cytochrome C, methylene blue or potassium ferricyanide. Furthermore, in the method (2), when catalase is used, H₂O₂ generated in process b is decomposed and generated NADH₂ can preferably be measured.

In the above methods, consumed oxygen can preferably be measured by electrochemical means using an oxygen electrode. Generated H₂O₂ can be measured by a hydrogen peroxide electrode or a hydrogen peroxide indicator. For example, a hydrogen peroxide coloring reagent which indicates the color changes in visible light, a hydrogen peroxide fluorescent reagent which shows fluorescence in ultraviolet light, or a hydrogen peroxide emission reagent can be used. A hydrogen peroxide coloring reagent, such as a combination of a peroxidase and a chromagen, is preferred. A preferred example is horseradish peroxidase (EC 1.11.1.7) using more than 0.05 unit per test, preferably 0.1–500 units. An example of a chromagen is a combination of an electron acceptor and a coupler at a concentration of over 0.1 mM.

Examples of electron acceptores are 4-aminoantipyrine, 4-amino-3-hydrazino-5-mercapto-1,2,4-triazole, 2-hydrozinobenzotriazole, 3-methyl-2-benzothiazolidone and 2-aminobenzothiazole.

Examples of couplers are phenol, 3-methyl-N-ethyl-N-(β-hydroxyethyl)-aniline, p-hydroxybenzoic acid, p-chlorophenol, 2,4-dichlorophneol, 4,6-dichloro-o-cresol, 2,4-dibromophenol, 3,5-dichloro-2-hydroxybenzenesulfonate, N,N-diethyl-m-toluidine, N,N-dimethyl-m-methoxyaniline, N-ethyl-N-sulfopropyl-m-toluidine, N-ethyl-N-(3-methylphenyl)-N'-acetylethylenediamine, 3-acetamino-N,N-diethylaniline, 3,5-xylenol and N,N-dimethylaniline. Fluorescent substrates are known substances such as bis(2,4,6-trichlorophneol) oxalate, phenylthiokyantoin, homovanillic acid, 4-hydroxyphenyl acetic acid, vanillylamine, 3-methoxytyramine, phloretin, hordenin, luminol monoamine and lucigenine, and can be used together with an electron acceptor. Reduced NAD and NADP [hereinafter designated as reduced NAD(P)] can be measured by absorbency at 340 mm or by colorimetry using a coloring reagent for reduced NAD(P). Coloring reagents for reduced NAD (P) are reagents for formazane pigment formation using diaphorase (NADH) (EC 1.6.9.9) or diaphorase (NADPH) (EC 1.6.9.9), using more than 0.01 unit, preferably 0.1–10 units and more than 0.01 mM, preferably 0.05–0.5 ml, of tetrazolium salt. Examples of tetrazolium salts are nitroblue tetrazolium chloride, 3-(4',5'-dimethyl triazolyl)-2,4-diphenyl-tetrazolium bromide, 2-(p-iodophenyl)-3-(p-nitrophenyl)-5-phenyl-tetrazolium chloride, 2,2',5,5'-tetra-(p-nitrophenyl)-3,3'(3-dimethoxy-4-phenylene)-ditetrazolium chloride, 2,3,5-triphenyltetrazolium chloride and neotetrazolium chloride. Diaphorase can be replaced by phenazine methosulfate, 8-dimethylamino-2,3-benzophenoxadine or 1-methoxy-5-methylphenazium-methyl sulfate. The amount of generated NH₃ can be measured by an ammonium electrode or an ion electrode. Also generated CO₂ can be measured by electrochemical means.

These reagents for assaying fatty acids or glycerol, electrochemical means, other reagents and compositions containing 1,2-diglycerides and nonionic surface active agents, are assembled in a suitable way. To a composition which contains a 1,2-diglyceride and a nonionic surface active agent is preferably added sodium deoxycholate and colipase. Lipase activity can be measured by adding this reagent and enzyme. The concentration of deoxycholate is preferably more than 0.5 mM in a substrate solution for lipase and is preferably 1-20 mM and 0.1-0.5 ml per assay. The amount of colipase to be added is 500 units or more per assay, preferably 2000-4000 units. A substrate solution for lipase can optionally be prepared by mixing the composition containing the 1,2-diglyceride, the nonionic surface active agent, and preferably deoxycholate and colipase, reagents for measuring fatty acids or glycerol, and reagents necessary for measuring the detectable changes by spectrophotometry. The amount of the composition containing the 1,2-diglyceride and the nonionic surface active agent is optionally 1/5-1/20 in a substrate solution, and more than 0.5 mM, preferably 1.5-5 mm, for the monoglyceride or 1,2-diglyceride and more than 0.1%, preferably 0.2-0.5%, for the nonionic surface active agent.

Examples of the composition containing the substrate are as follows:

A composition containing ATP, CoASH, deoxycholate, colipase, acyl-CoA synthetase, acyl-CoA oxidase, a 1,2-diglyceride, a nonionic surfacce active agent and a hydrogen peroxide coloring reagent, and preferably an SH reagent such as maleimide, N-methylmaleimide, N-ethylmaleimide or N-phenylmaleimide; a composition containing ATP, CoASH, deoxycholate, colipase, acyl-CoA synthetase, accyl-CoA oxidase, enoyl-CoA hydratase, 3-hydroxyacyl-CoA dehydrogenase, 3-ketoacyl-CoA thiolase, a 1,2-diglyceride, a nonionic surface active agent and NAD(P), a preferably catalase, flavine adenine dinucleotide and NAD(P) coloring reagents; a composition containing magnesium chloride, ATP, deoxycholate, colipase, glycerol kinase, glycerophosphate oxidase, a 1,2-diglyceride, a nonionic surface active agent and a hydrogen peroxide coloring reagent; a composition containing magnesium chloride, ATP, deoxycholate, colipase, glycerol kinase, glycerophosphate dehydrogenase, a 1,2-diglyceride, a nonionic surface active agent, and a hydrogen acceptor; and a composition containing deoxycholate, colipase, glycerol dehydrogenase, NAD(P), a 1,2-diglyceride, a nonionic surface active agent, and an NAD(P) coloring reagent.

The amount and concentration of the reagents used are illustrated as follows:

ATP and CoASH: at least several times molar excess, such as 0.5-50 $\mu$M, 0.05 $\mu$mol/test, preferalby more than 2 $\mu$moles.

NAD(P): 0.5-50 mM solution, more than 0.05 $\mu$mole, preferably more than 2 $\mu$moles/test.

Magnesium chloride: 5-50 mM solution, 0.1-0.5 ml/test.

Acyl-CoA synthetase: more than 0.1 u, preferably 0.5-1 u/test.

Acyl-CoA oxidase: more than 1 u, preferably 5-20 u/test.

Enoyl-CoA hydratase, 3-hydroxyacyl-CoA dehydrogenase and 3-ketoacyl-CoA thiolase: more than 0.1 u, preferably 1-25 u/test.

Glycerol kinase: more than 0.01 u, preferably 0.05-t u/test.

Glycerophosphate oxidase: more than 0.5 u, preferably 1-20 u/test.

Glycerol dehydrogenase: more than 0.5 u, preferably 1-20 u/test.

These reagents are used by dissolving in a buffer solution of pH 7-9. Examples of buffer solutions are 10-500 mM solutions of phosphates, glycylglycine, Tris-HCl, dimethyl glutarate, imidazole-HCl, Good's solution such as PIPES-NaOH, or a glycine buffer.

The above concentrations and amounts are illustrative and can optionally be altered. Furthermore, if required, NaCl, a stabilizer for enzymes, or a preservative can be added. The other required treatment should optionally be performed, if necessary, For example, in the method (1) hereinbefore, generated hydrogen peroxide may be reacted with a reductant such as CoASH remaining from the previous process, and so the said reamining CoASH should preferably be blocked by an SH reagent. For this reason, each reagent of the process a, b or c is preferably prepared separately.

As hereinabove explained, a composition for lipase assay containing a 1,2-diglyceride and a nonionic surface active agent, more preferably a composition further containing deoxycholate and colipase, or more preferably a composition containing a reagent for measuring fatty acid or glycerol therein and a substrate composition optionally containing a reagent measuring the detectable changes therein, can be prepared. These compositions are usually used in an amount of 0.1-5 ml per assay for 0.1-5 ml of the specimen at 37° C. for one minute or more. Lipase activity in the speciment can be assayed by measuring the finally appearing detectable changes by means of spectrometry of by electrochemical means. In general, homogeneous aqueous solution having absorption ratio in optical density of less than 0.5, preferably less than 0.3 at 340 nm is used for an assay.

The composition for lipase assay of the present invention has a number of advantages, for example no phase separation, stability, no turbidity and reproducibility of assay.

The following example illustrates the present invention but is not to be construed as limiting.

EXAMPLE (1) Preparing compositions for lipase assay:

A number of different glycerides, as substrates for lipase assay, were added to an aqueous solution (10 ml) or 2-5 (w/v) of a nonionic surface active agent and heated at 37° C. for 30 minutes for solubilization to prepare a 20 mM concentration of substrate solution. Commerically available glycerides in organic solvents were used, after removing off the solvent in a rotary evaporator. Triglycerides were mixed with nonionic surface active agents and treated by ultra sonication to prepare the emulsion.

(2) Measuring the turbidity:

A substrate solution for lipase assay comprising a 20 mM substrate solution prepared as in (1) herienabove (100 $\mu$l), 0.1 M PIPES-NaOH buffer solution (pH 7.5, 200 $\mu$l, 2 M NaCl (100 $\mu$l), 50 mM MgCl$_2$ (30 $\mu$l), 120 mM Na deoxycholate (25 $\mu$l) and distilled water (545 $\mu$l) was prepared and the absorbency was measured at 340 nm (A$_{340}$ nm).

The results are shown in Table 1.

As a result, 1,3-dioleoyl-glycerols and trioleoyl-glycerols shown higher absorbency as compared with 1,2-diglycerides such as 1,2-dioleoylglycerol and 1-linoleoyl-2-palmitoylglycerol, and are disadvantageous for the spectrometric assay of lipase. On the contrary, 1,2-diglycerides have higher transparency of absorbance less than 0.5, preferably less than 0.3 at 340 nm due to good solubility in water.

(3) Lipase assay using a 1,2-diglyceride as a substrate:

| Reaction solution I: | |
|---|---|
| 0.2 M PIPES-NaOH buffer (pH 7.5) | 0.20 ml |
| 2 M NaCl | 0.10 ml |
| 50 mM MgCl$_2$ | 0.025 ml |
| 20 mM ATP | 0.05 ml |
| 50 mM CoASH | 0.025 ml |
| 12 mM Na deoxycholate | 0.25 ml |
| colipase (Boehringer, 27,000 U/ml) | 0.10 ml |
| 18 mM 1,2-dioleoylglycerol containing 3.5% Nonidet P-40 solution | 0.10 ml |
| Acyl-CoA synthetase (Toyo Jozo Co., 10 U/ml) | 0.10 ml |
| distilled water | 0.05 ml |
| Total | 1.00 ml |
| Reaction solution II: | |
| 0.2 M PIPES-NaOH buffer (pH 7.5) | 0.1 ml |
| 0.3% 4-aminoantipyrine | 0.3 ml |
| 0.2% phenol | 0.3 ml |
| peroxidase (Sigma Co., 45 U/ml) | 0.1 ml |
| 1% Triton X-100 | 0.1 ml |
| Acyl-CoA oxidase (Toyo Jozo Co., 150 U/ml) | 0.1 ml |
| distilled water | 0.5 ml |
| Total | 1.5 ml |

TABLE 1

| glyceride | nonionic surface active agent | A$_{340\ nm}$ |
|---|---|---|
| The present invention | | |
| 1-capryl-2-palmitoleyl-glycerol | Nonidet P40 (POE alkylaryl ether) | 0.094 |
| 1-capryl-2-linolenoyl-glycerol | Nonidet P40 (POE alkylaryl ether) | 0.079 |
| 1-oleoyl-2-caprylyl-glycerol | Nonidet P40 (POE alkylaryl ether) | 0.083 |
| 1-capryl-2-oleoyl-glycerol | Nonidet P40 (POE alkylaryl ether) | 0.091 |
| 1,2-dioleoyl-glycerol | Nonidet P40 | 0.101 |
| 1,2-dioleoyl-glycerol | Triton X-100 | 0.105 |
| 1,2-dioleoyl-glycerol | Nonion NS-220 | 0.100 |
| 1,2-dioleoyl-glycerol | NIKKOL OP-10 | 0.102 |
| 1,2-dioleoyl-glycerol | Pluronic L122 | 0.125 |
| 1-linoleoyl-2-palmitoyl-glycerol | Nonidet P40 | 0.107 |
| 1-linoleoyl-2-palmitoyl-glycerol | Triton X-100 | 0.109 |
| 1-linoleoyl-2-palmitoyl-glycerol | Nonion NS-220 | 0.099 |
| 1-linoleoyl-2-palmitoyl-glycerol | NIKKOL OP-10 | 0.086 |
| 1-linoleoyl-2-palmitoyl-glycerol | Pluronic L122 | 0.269 |
| Control | | |
| 1,3-dioleoyl-glycerol | Brij 98 | 1.74 |
| 1,3-dioleoyl-glycerol | Nonidet P40 | 1.76 |
| 1,3-dioleoyl-glycerol | Triton X-100 | 1.74 |
| 1,3-dioleoyl-glycerol | Nonion P-10 | 1.69 |
| 1,3-dioleoyl-glycerol | Nonion ST-221 | 1.80 |
| 1,3-dioleoyl-glycerol | Tween 80 | 1.78 |
| 1,3-dioleoyl-glycerol | Pluronic L122 | 1.86 |
| trioleoyl-glycerol | Brij 98 | 2.49 |
| trioleoyl-glycerol | Nonidet P40 | 2.44 |
| trioleoyl-glycerol | Triton X-100 | 2.34 |
| trioleoyl-glycerol | Nonion P-10 | 2.37 |
| trioleoyl-glycerol | Tween 80 | 2.47 |
| trioleoyl-glycerol | Pluronic L122 | 2.68 |

Porcine pancreas lipase (0.15 U/ml, by the olive oil emulsion method) (20 μl) was added to the reaction solution I and the mixture was incubated at 37° C. for 10 mins. 20 mM n-ethylmaleimide (0.5 ml) was added thereto to stop the reaction. Oleic acid liberated from the 1,2-diglyceride was assayed as follows:

Reaction solution II (1.5 ml) was added to the above reaction mixture and the mixture was incubated at 37° C. for 5 mins., then the absorbency was measured at 500 nm (O.D.$_{500\ nm}$=0.076) which showed a lipase activity of 0.19 U/ml.

(4) Lipase assay using 1,2-diglyceride:

| 0.4 M PIPES-NaOH buffer (pH 7.5) | 0.1 ml |
|---|---|
| 2 M NaCl | 0.1 ml |
| 50 mM MgCl$_2$ | 0.025 ml |
| 100 mM ATP | 0.01 ml |
| 50 mM NAD | 0.025 ml |
| 50 mM CoASH | 0.025 ml |
| 12 mM Na deoxycholate | 0.25 ml |
| colipase (Boehringer, 27,000 U/ml) | 0.10 ml |
| 18 mM 1-linoleoyl-2-palmitoyl glycerol (dissolved in 3.5% Nonidet P-40 solution) | 0.10 ml |
| Acyl-CoA synthetase (Toyo Jozo Co., 300 U/ml) | 0.05 ml |
| HDT (multi-active enzyme comprising enoyl-CoA hydratase, 3-hydroxy-CoA dehydrogenase and 3-ketoacyl-CoA thiolase: dehydrogenase 400 U/ml) | 0.02 ml |
| 1 mM FAD | 0.02 ml |
| distilled water | 0.175 ml |
| Total | 1.00 ml |

The above 1-linoleoyl-2-palmitoyl glycerol was prepared by reacting trilinoleoyl-2-palmitoyl-sm-glycero-3-phosphoryl-choline (Nippon Shoji Co., synthetic phospholipid) with phospholipase C (Toyo Jozo Co.)

Porcine pancreatic lipase (0.15 U/ml, 20 μl) was added to the above reaction mixture (1.00 ml), which was then incubated at 37° C. and the generated reduced NAD was continuously measured at 340 nm. The increase in absorbency relative to reaction time was observed and the increase in optical density was 0.082/min.

In the above reaction, linoleic acid was liberated from the 1,2-diglyceride by pancreatic lipase action and a 5-molar ratio of reduced NAD was generated by a cycling reaction of acyl-CoA synthetase, acyl-CoA oxidase and HDT. The amount of linolic acid is calculated by the mmole coefficient (6.1) of reduced NAD×5-molar ratio=30.5 and the lipase activity is measured by the following equation:

$$\text{lipase activity } (U/ml) = 0.082 \times \frac{1}{30.5} \times \frac{1000}{20} = 0.13$$

(5) Lipase assay using a 1,2-diglyceride from phospholipase C and lecithin:

| 0.2 M dimethyl glutarate-NaOH buffer (pH 7.5) | 0.2 ml |
|---|---|
| 15 mM linoleoyl-2-palmitoyl lecithin (dissolved in 3.7% Nikkol OP-10) | 0.1 ml |
| phospholipase C (50 U/ml, Toyo Jozo Co.) | 0.05 ml |
| acyl-CoA synthetase (10 U/ml) | 0.1 ml |
| 50 mM MgCl$_2$ | 0.03 ml |
| 12 mM Na Deoxycholate | 0.25 ml |
| colipase (27,000 U/ml) | 0.1 ml |
| 20 mM CoASH | 0.05 ml |
| 10 mM ATP | 0.05 ml |
| distilled water | 0.07 ml |
| Total | 1.0 ml |

The reaction mixture hereinabove (1.0 ml) was incubated at 37° C. for 30 mins. to generate 1,2-diglyceride (1-linoleoyl-2-palmitoyl glycerol) from 1-linoleoyl-2-palmitoyl lecithin by the action of phospholipase C. Lipase (0.6 U/ml, assayed by olive oil Adekatol SO-120 emulsion, 20 μl) obtained from *Chromobacterium viscosum* was added thereto and the mixture was incubated at 37° C. for 10 mins. The reaction was stopped by adding 20 mM ethylmaleimide (0.5 ml). The reaction mixture II, (3) hereinbefore (1.5 ml) was added thereto and the mixture was incubated at 37° C. for 5 mins., then the absorbency was measured at 500 nm to obtain O.D.=0.091 whereby lipase activity was defined as 0.23 U/ml.

(6) Lipase assay using a 1,2-diglyceride from phosphatidate phosphatase and phosphatidate:

| | |
|---|---|
| 0.2 M Tris-HCl buffer (pH 7.5) | 0.2 ml |
| 20 mM phosphatidate (dissolved in 4% Nonidet P-40) | 0.1 ml |
| phosphatidate phosphatase (13 U/ml) | 0.1 ml |
| acyl-CoA synthetase (20 U/ml) | 0.05 ml |
| 50 mM MgCl$_2$ | 0.03 ml |
| 20 mM CoASH | 0.05 ml |
| 10 mM ATP | 0.05 ml |
| 12 mM Na deoxycholate | 0.25 ml |
| colipase (27,000 U/ml) | 0.10 ml |
| distilled water | 0.07 ml |
| Total | 1.0 ml |

The reaction mixture (1.0 ml) hereinabove was incubated at 37° C. for 10 mins. to generate a 1,2-diglyceride from phosphatidate by phosphatidate phosphatase.

Porcine pancreatic lipase (0.15 U/ml, 20 μl) was added to the reaction mixture and the mixture was incubated at 37° C. for 10 mins. 20 mM N-ethylmaleimide (0.5 ml) was added to stop the reaction. The generated fatty acid was colored by adding the reaction mixture II (3) hereinbefore and the absorbency was measured at 500 nm to obtain O.D.$_{500\ nm}$=0.080, whereby lipase activity was defined as 0.20 U/ml.

What is claimed is:

1. An assay method for lipase activity comprising the steps of: contacting a specimen for lipase activity to be assayed with a homogeneous aqueous solution having an optical density below 0.5 at 340 nm, containing at least 0.5 mM of a 1,2-diglyceride comprising two higher fatty acid moieties of 8 or more carbon atoms, said diglyceride selected from the group consisting of 1-linoleoyl-2-lauroyl-glycerol, 1-linoleoyl-2-myristoryl-glycerol, 1-linoleoyl-2-palmitoyl-glycerol, 1-linoleoyl-2-stearoyl-glycerol, [1-linolenoyl-2-lauroyl-glycerol, 1-linolenoyl-2-myristoyl-glycerol, 1-linolenoyl-2-palmitoyl-glycerol, 1-linolenoyl-2-stearoyl-glycerol,] 1,2-dilinoleoyl-glycerol, [1,2-dilinolenoyl-glycerol,] 1-linoleoyl-2-caprylyl-glycerol, and 1-linoleoyl-2-capryl-glycerol, and at least 0.1% of a nonionic surface active agent of more than HLB 10; and measuring the thus-liberated glycerol or higher fatty acid.

2. An assay method according to claim 1 wherein said 1,2-diglyceride is generated from a reaction with phospholipase C and lecithin, phosphatidate phosphate and phosphatidic acid, or phospholipase, D, phosphatidate phosphatase and lecithin.

3. An assay method according to claim 1 wherein said nonionic surface active agent is a polyoxyethylene nonionic surface active agent, a polyhydric alcohol nonionic surface active agent, or a block polymer nonionic surface active agent.

4. An assay method according to claim 3 wherein said polyoxyethylene nonionic surface active agent is selected from the group consisting of: polyoxyethylene aliphatic alcohol ethers, polyoxyethylene alkylaryethers, polyoxyethylene fatty acid esters, polyoxyethylene sorbitan fatty acid esters, polyoxyethylene sorbitol fatty acids, polyoxyethylene caster oil derivatives and polyoxyethylene hardening caster oil derivatives.

5. An assay method according to claim 3 wherein said polyhydric alcohol nonionic surface active agent comprises an ester formed from a polyhydric alcohol selected from the group consisting of sorbitan, mannitol, sorbitol and sucrose, and a higher fatty acid of 8 or more carbons.

6. An assay method according to claim 3 wherein said block polymer nonionic surface active agent has polypropylene blocks and polyoxyethylene blocks.

7. An assay method according to claim 1, which further comprises the step of assaying the said liberated higher fatty acid using a reagent comprising adenosine triphosphate, coenzyme A, deoxycholate, colipase, acyl-CoA synthetase, acyl-CoA oxidase and hydrogen peroxide coloring reagent.

8. An assay method according to claim 1, which further comprises the step of assaying the said liberated higher fatty acid using a reagent comprising adenosine triphosphate, coenzyme A, deoxycholate, colipase, acyl-CoA synthetase, acyl-CoA oxidase, enol-CoA hydratase, 3-hydroxyacyl-CoA dehydrogenase, 3-ketoacyl-CoA thiolase and nicotine adenine dinucleotide.

9. An assay method according to claim 1, which further comprises the step of assaying said liberated glycerol using a reagent comprising magnesium chloride, adenosine triphosphate, deoxycholate, colipase, glycerol kinase, glycerophosphate oxidase and hydrogen peroxide coloring reagent.

10. An assay method according to claim 1, which further comprises the step of assaying said liberated glycerol using a reagent comprising magnesium chloride, adenosine triphosphate, deoxycholate, colipase, glycerol kinase, glycerophosphate dehydrogenase and hydrogen acceptor.

11. An assay method according to claim 1, which further comprises the step of assaying said liberated glycerol using a reagent comprising deoxycholate, colipase, glycerol dehydrogenase and nicotine adenine dinucleotide.

* * * * *